United States Patent [19]

Douglas et al.

[11] Patent Number: 5,180,090

[45] Date of Patent: Jan. 19, 1993

[54] BOTTLE CAP WITH DENTAL FLOSS DISPENSER

[75] Inventors: Jerry A. Douglas, Harrisburg, Ill.; Walter R. Pfitzinger, St. Charles, Mo.

[73] Assignee: 7L Corporation, Harrisburg, Ill.

[21] Appl. No.: 659,900

[22] Filed: Feb. 25, 1991

[51] Int. Cl.5 .................. B65H 75/32; A61C 15/04
[52] U.S. Cl. ................................. 225/42; 225/6; 225/77; 225/90
[58] Field of Search ............... 242/138, 141, 137.1, 242/146; 225/6, 32, 42, 80, 90, 77; 132/324

[56] References Cited

U.S. PATENT DOCUMENTS

| | | | |
|---|---|---|---|
| 1,439,076 | 12/1922 | Edwards | 225/6 |
| 1,858,134 | 5/1932 | Booth et al. | 225/6 |
| 1,981,388 | 11/1934 | Perry | 225/80 |
| 3,246,815 | 4/1966 | Aronson | 225/44 |
| 4,290,223 | 9/1981 | Ostenberg et al. | 242/137.1 |
| 4,327,755 | 5/1982 | Endelson | 132/324 |

Primary Examiner—Hien H. Phan
Attorney, Agent, or Firm—Polster, Lieder, Woodruff & Lucchesi

[57] ABSTRACT

A cap for a bottle of mouth wash or the like is disclosed having a floss dispenser on the top thereof. The floss dispenser includes spool of floss and a knife on the outer surface of the dispenser. The dispenser has a lower half and an upper half hingedly connected to the lower half so that the dispenser may be opened to removably receive the spool of floss. A shield which surrounds the knife also serve as a fingerhold which may be pushed upwardly to open the dispenser.

2 Claims, 1 Drawing Sheet

BOTTLE CAP WITH DENTAL FLOSS DISPENSER

BACKGROUND OF THE INVENTION

This invention relates to a bottle cap and more particularly to a bottle cap for mouthwash, toothpaste, or the like which includes a floss dispenser.

Flossing teeth is known to be beneficial to the care of one's teeth. However, floss is often kept in medicine cabinets or bathroom drawers separate from tooth paste and mouthwash. Because the floss is out of sight, it is often forgotten by those who are not in the habit of flossing regularly. It is thus desirable to keep dental floss with the toothpaste or mouthwash.

SUMMARY OF THE INVENTION

It is one object of the invention to provide a device which will keep dental floss in close proximity to toothpaste or mouthwash so as to encourage flossing.

Another object is to provide a dental floss dispenser which may be refilled with dental floss when a spool of floss is fully used.

Still another object of this invention is to provide a floss dispenser which may readily be used before or after flossing or brushing, which is inexpensive to manufacture, and which is easy to use.

These and other objects will become apparent to those skilled in the art in light of the following disclosure and accompanying drawings.

In accordance with the invention, generally stated, a bottle cover or cap of the present invention includes a cap which may be removably received (screwed) on a bottle to close the bottle and a floss container incorporated in the cap. The floss container includes a spool of floss rotatably received in the container, an exit through which the floss may be threaded to be pulled from the container, and knife means carried by the cap for cutting the floss to a desired length. The floss container has an upper portion and a lower portion which are hinged together so that the floss container may be opened and closed. The knife means include a blade, an upper shield above the blade and a lower shield below the blade. The upper and lower shields are preferably somewhat wider and longer than the blade so that a user's finger cannot contact the blade. The floss container further includes means on the upper portion for holding the upper portion in its closed position which is manually operable to facilitate opening of the floss container to facilitate replacement of the floss spool.

Other objects and features of this invention are in part apparent and are in part pointed out hereinafter

BRIEF DESCRIPTION OF THE DRAWINGS

Corresponding reference characters indicate corresponding parts throughout the several views of the drawings.

DESCRIPTION OF THE PREFERRED EMBODIMENT

Figure 1:
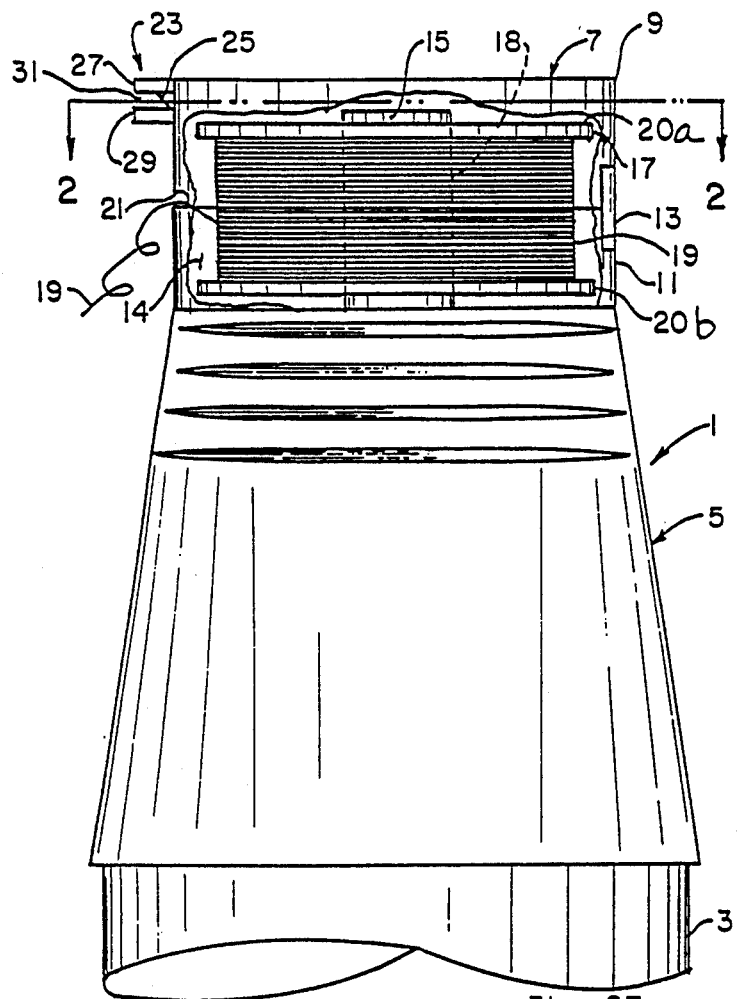
FIG. 1 is a front elevational view, partially cut away, of a bottle cap of the present invention having a floss dispenser thereon.

Referring to the drawings, a cover of the present invention is indicated in its entirety at 1 for a bottle 3. Cover 1 is shown to include a cap 5 and a floss dispenser 7 attached to the top thereof. Cap 5 is removably, sealably received (threaded) on the neck of bottle 3.

Figure 3:
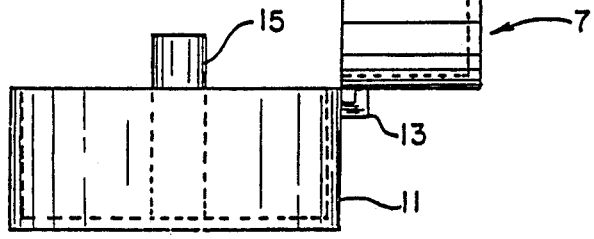
FIG. 3 is a side elevational view of the dispenser when opened.

Dispenser 7 includes an upper portion 9 hingedly connected to a lower portion 11 by a hinge 13 for movement between a closed position (as shown in FIG. 1) and an open position (as shown in FIG. 3). Hinge 13 is preferably of the type which "snaps" open and closed and cannot be moved without an external force, such as an upward manual push. When closed, the upper and lower portions define a cavity 14. A cylindrical core or spindle 15 mounted on lower portion 11 rotatably receives a floss spool 17 containing a quantity of floss 19. Spool 17 includes a spool body 18 having a spool bore B therethrough and upper and lower circular spool ends or plates 20a, 20b integral therewith. Floss 19 is wound about spool body 18 between plates 20a, 20b.

The upper portion 9 of dispenser 7 includes an opening or exit 21 through which floss 19 is threaded so that the floss is accessible from the exterior of the dispenser 7. The ability to open and close the dispenser 7 allows for the floss to be extricated from cavity 14 when the floss falls into cavity 14, and it also allows for the floss spool 17 to be replaced with a new spool of floss when the floss is used up.

Figure 2:
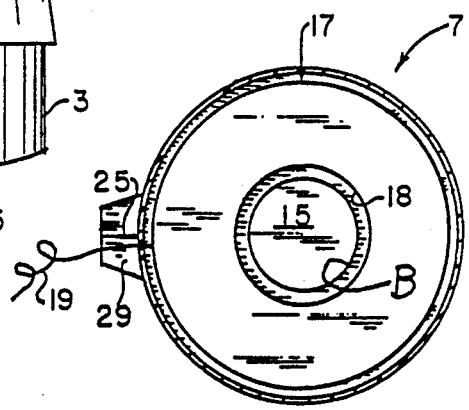
FIG. 2 is a cross-sectional view of the floss dispenser taken along line 2—2 of FIG. 1.

A knife assembly 23 is rigidly mounted on dispenser 7 so that the user may cut off a desired length of floss 19 for use. Knife assembly 23 includes a blade 25 for cutting the floss pulled from spool 17 through opening 21. An upper shield 27 and a lower shield 29 surround blade 25. Shields 27 and 29 are preferably trapezoidal in shape, as shown in FIG. 2, and are wider and longer than blade 25 so that blade 25 cannot inadvertently cut a user's fingers. Shields 27 and 29 are vertically spaced apart so as to provide a channel 31 therebetween, open on three sides through which the floss may be passed so that it may be cut by blade 25.

As shown in FIG. 1, when upper portion 9 is in its closed position, shields 27 and 29 project out from the sides of the upper portion thus providing a fingerhold against which a user may place his finger or thumb to facilitate opening of dispenser 7.

Numerous variations within the scope of the appended claims will be apparent to those skilled in the art in light of the foregoing description and accompany drawings. For example, cap 5 and dispenser 7 may be designed so that dispenser 7 may be removably connected to cap 5. This would allow for floss dispenser 7 to be attached to a new bottle should the bottle to which it was originally connected be emptied before the floss is used. It would also allow for the connection of a new floss dispenser should the floss be used up before the contents of the bottle are emptied. These variations are merely illustrative.

In view of the above, it will be seen that the various objects and features of this invention are achieved and other advantageous results obtained.

As various changes could be made in the above constructions without departing from the scope of the invention, it is intended that all matter contained in the above description or shown in the accompanying drawing shall be interpreted as illustrative and not in a limiting sense.

We claim:
1. A bottle cover comprising:
   a cap which may be removably received on a bottle to close the bottle, said cap including an upper portion and a lower portion hinged together so that said cap may be opened and closed;

a floss chamber within said cap, said floss chamber receiving a spool of floss received in said chamber;

an exit in said cap through which said floss may be threaded to be pulled from said chamber;

means for cutting said floss to a desired length including a knife blade, an upper shield above said knife blade and a lower shield below said knife blade, said upper and lower shields spaced apart above and below said knife blade so as to expose said knife blade therebetween for cutting said floss, said upper and lower shields further being wider and longer than said blade so as to protect the user against being cut by said knife blade; and means cooperable with said upper portion for holding said upper and lower portions closed;

said upper portion including means for facilitating opening of said floss container comprising said lower shield of said knife means.

2. A dental floss dispenser which receives a spool of dental floss, said dispenser comprising:

an upper portion and a lower portion, said upper and lower portions being hingedly connected together and movable between an open and a closed position, said upper and lower portions defining a chamber, and a core extending upward from a bottom of said lower portion within said chamber, said spool being rotatably received on said core;

knife means for cutting said floss, said knife means including a knife, an upper shield above said blade and a lower shield below said blade, said upper and lower shields being spaced apart from one another for cutting of said floss on said blade and being wider and longer than said blade so as to protect the user against inadvertently being cut; and clasp means for holding said upper and lower portions closed, and push means comprising said lower shield of said knife means for enabling the ready manual opening of said upper and lower portions of said dispenser.

* * * * *